US007758851B2

(12) United States Patent  
Urgell Beltran et al.

(10) Patent No.: US 7,758,851 B2
(45) Date of Patent: Jul. 20, 2010

(54) PRESERVATIVE SYSTEMS AND THEIR USE IN COSMETIC PREPARATIONS

(75) Inventors: Joan Baptista Urgell Beltran, Barcelona (ES); Joan Seguer Bonaventrua, Barcelona (ES)

(73) Assignee: Laboratorios Miret, S.A., Barcelona (ES)

( * ) Notice: Subject to any disclaimer, the term of this patent is extended or adjusted under 35 U.S.C. 154(b) by 0 days.

(21) Appl. No.: 10/484,226

(22) PCT Filed: Aug. 9, 2001

(86) PCT No.: PCT/EP01/09200

§ 371 (c)(1),
(2), (4) Date: Jan. 16, 2004

(87) PCT Pub. No.: WO03/013454

PCT Pub. Date: Feb. 20, 2003

(65) Prior Publication Data

US 2004/0166082 A1    Aug. 26, 2004

(51) Int. Cl.
*A61K 8/00* (2006.01)
(52) U.S. Cl. ............... 424/70.19; 424/70.27; 424/70.31
(58) Field of Classification Search ............... 424/70.21
See application file for complete search history.

(56) References Cited

U.S. PATENT DOCUMENTS

| 3,825,560 | A | 7/1974 | Saito et al. ............. 260/326.45 |
| 4,389,489 | A | 6/1983 | Preiss et al. ................... 435/280 |
| 5,336,515 | A | 8/1994 | Murphy et al. ............... 426/573 |
| 5,661,149 | A * | 8/1997 | King et al. ................... 514/241 |
| 5,681,802 | A * | 10/1997 | Fujiwara et al. ............. 510/130 |
| 5,780,658 | A | 7/1998 | Martinez-Pardo et al. ..... 554/51 |
| 6,068,867 | A | 5/2000 | Nussinovitch et al. ...... 426/102 |
| 6,087,400 | A * | 7/2000 | Dyer et al. ................... 514/643 |
| 6,299,915 | B1 | 10/2001 | Nussinovitch et al. ........ 426/89 |
| 7,074,447 | B2 | 7/2006 | Bonaventura et al. |
| 2003/0049305 | A1 | 3/2003 | Von Rymon Lipinski et al. .......................... 424/439 |
| 2004/0166082 | A1 | 8/2004 | Urgell-Beltran et al. . 434/70.21 |
| 2004/0175350 | A1 | 9/2004 | Urgell Beltran et al. .. 424/70.27 |
| 2004/0265443 | A1 | 12/2004 | Beltran et al. ............... 426/321 |
| 2005/0175747 | A1 | 8/2005 | Seguer Bonaventura et al. .......................... 426/323 |
| 2006/0003421 | A1 | 1/2006 | Markussen et al. ......... 435/69.1 |

FOREIGN PATENT DOCUMENTS

| DE | 1 226 745 | 10/1966 |
| EP | 0 485 616 A1 | 5/1992 |
| EP | 0 500 332 | 8/1992 |
| EP | 0 749 960 A1 | 12/1996 |
| FR | 2.143.557 | 2/1973 |
| GB | 1 352 420 | 5/1974 |
| JP | 48-17047 | 3/1973 |
| JP | 58039651 | 3/1983 |
| JP | 59-164704 | 9/1984 |
| JP | 03-291211 | 12/1991 |
| JP | 09-188605 | 7/1997 |
| JP | 09-255518 | 9/1997 |
| JP | 09-286712 | 11/1997 |
| JP | 10045557 | 2/1998 |
| WO | WO94/19027 | * 2/1993 |
| WO | 94/07377 | 4/1994 |
| WO | WO 94/09027 | 9/1994 |
| WO | WO 94/19026 | * 9/1994 |
| WO | WO 94/19027 | * 9/1994 |
| WO | WO9418027 | * 9/1994 |
| WO | WO9419027 | * 9/1994 |
| WO | 96/21642 | 7/1996 |
| WO | 97/30964 | 8/1997 |

(Continued)

OTHER PUBLICATIONS

Chemical Abstracts No. 103:179968; *A Comparative Study on Surface-Active and Antimicrobila Properties of Some N.alpha-lauroyl-L-alpha, omega-dibasic amino acid derivatives* (1985).

Chemical Abstracts Service, Columbus, Ohio, US; Garcia Dominguez, J. et al.: "Cationic Surfactants With Antimicrobial Activity" retrieved from STN Database Accession No. 107:79974, XP002196810, Abstract and ES 530 051 A (Consejo Superior De Investigaciones Cientificas, Spain) May 1, 1995.

(Continued)

*Primary Examiner*—Robert A Wax
*Assistant Examiner*—Melissa S Mercier
(74) *Attorney, Agent, or Firm*—Renner, Otto, Boisselle & Sklar, LLP

(57) ABSTRACT

The invention relates to preservative systems which are particularly suitable in cosmetic and dermatological preparations. The preservative system which comprises a cationic surfactant, derived from the condensation of fatty acids and esterified dibasic amino acids, having the formula (I) where: $X^-$ is $Br^-$, $Cl^-$, or $HSO_4$ $R_1$: is a straight alkyl chain from an acid or saturated fatty hydroxy acid from 8 to 14 atoms of carbon bonded to the α-amino acid group through amidic bond. $R_2$: is a straight or branched alkyl chain from 1 to 18 carbon atoms or aromatic. $R_3$: is: (II) where n can be from 0 to 4, is combined with at least one other ionic or non-ionic preservative agent, whereby the combination displays a synergetic activity. A preservative system, wherein the cationic surfactant preservative derived from the condensation of fatty acids and esterified dibasic amino acid is LAE is particularly preferred. The other ionic or non ionic preservative agent is preferably at least one component selected from the group consisting of 2-bromo-2-nitro-1,3-propanediol (bronopol), parbens, imidazolidinyl urea, phenoxyethanol, DMDM hydantoin, 2-methyl-5-chloro-3,4-isothiazolinone/2-methyl-3,4-isothiazolinone and quaternium-15.

10 Claims, No Drawings

FOREIGN PATENT DOCUMENTS

| | | | |
|---|---|---|---|
| WO | 01/49121 | | 7/2001 |
| WO | WO 03/013491 | * | 2/2003 |

OTHER PUBLICATIONS

Chemical Abstracts Service, Columbus, Ohio, US; Garcia Dominguez, J. J. et al.: "N.alpha.-Acyl-L-alkylaminoguanidinic Acids and Their Salts as Surfactants With Antimicrobial Action" retrieved from STN Database Accession No. 99:122920, XP002196912, Abstract and ES 512 643 A (Asociacion De Investigacion De Detergentes, Spain) Feb. 16, 1983.

Infante et al., Surface Active Molecules: Preparation and Properties of Long Chain Nα-ACYL-L-α-Amino-ω-Guanidine Alkyl Acid Derivatives; International Journal of Cosmetic Science 6, 1984, pp. 275-282.

Infante et al., A Comparative Study on Surface Active and Antimicrobial Properties of Some Nα-Lauroyl-Lα, ωDibasic Aminoacids Derivatives; Fette Seifen Anstrichmittel, No. 8, 1985, pp. 309-313.

Garcia Dominguez et al.; Monocapas De Algunos N-α-Acil Aminoacidos Antimicrobianos En Soluciones De NaCl; Anales de Quimica, vol. 82, 1986, pp. 413-418.

Infante et al.; The Influence of Steric Configuration of Some Nα-Lauroyl Amino-Acid Derivatives on Their Antimicrobial Activity; Fette Seifen Anstrichmittel, 88, No. 3, 1986, pp. 108-110.

Molinero et al.; Synthesis and Properties of Nα-Lauroyl-L-Argine Dipeptides From Collagen; JAOCS, vol. 65, No. 6, 1988, 4 pages.

Vinardell et al.; Comparative Ocular Test of Lipopeptidic Surfactants; International Journal of Cosmetic Science 12, 1990, pp. 13-20.

Kunieda et al.; Reversed Vesicles From Biocompatible Surfactants, Advanced Materials, No. 4, 1992, pp. 291-293.

Infante et al.; Sintesis Y Propiedades De Tensioactivos Cationicos Derivados De Arginina; Anales de Quimica, vol. 88, 1992, pp. 542-547.

Főrdedal et al.; Lipoamino Acid Association in the System Nα-Lauroyl-L-Arginine Methyl Ester—1-Pentanol—Water As Studied by Dielectric Spectroscopy; Colloids and Surfaces A: Physiochemical and Engineering Aspects, 79, 1993, pp. 81-88.

Infante et al., Non-Conventional Surfactants From Amino Acids and Glycolipids: Structure, Preparation and Properties; Colloids and Surfaces A: Physicochemical and Engineering Aspects 123-124, 1997, pp. 49-70.

Moran et al.; Chemical Structure/Property Relationship in Single-Chain Arginine Surfactants; Langmuir 2001, 17, pp. 5071-5075.

* cited by examiner

PRESERVATIVE SYSTEMS AND THEIR USE IN COSMETIC PREPARATIONS

RELATED APPLICATION DATA

This application is a continuation under 35 U.S.C. 371 of PCT/EP01/09200, filed Aug. 9, 2001.

FIELD OF THE INVENTION

This invention relates to new preservative systems for cosmetic preparations.

BACKGROUND OF THE INVENTION

Due to their composition, many cosmetic products are susceptible to act as a culture medium for micro-organisms, and this can possibly cause changes to the cosmetic preparation and constitute a risk to human heath as well. Thus, a cosmetic composition necessarily requires good protection against microbiological contamination. For this reason, a large number of preservatives to inhibit or reduce the microbial population is used.

Most of the systems currently used display incompatibilities with the human skin, such as irritations and allergies and are toxic to human beings as well. On the other hand, it has been demonstrated that cationic surfactants derived from lauric acid and arginine are protective substances against micro-organisms, in particular, the ethyl ester of the lauramide of the arginine monohydrochloride, hereafter referred to as LAE. LAE has the chemical structure of formula (1).

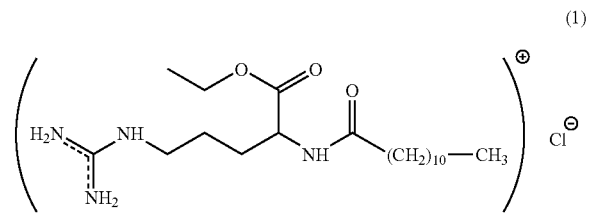

The compound LAE is remarkable for Its activity against different micro-organism, like the bacteria, fungi and yeast which can be present in cosmetic formulations and preparations, and its innocuity for humans.

It was the object of the present invention to provide further preservative systems for cosmetic preparations with in particular the goal of providing systems which comprise smaller amounts of the usual preservatives in view of the risk of lack of tolerance.

DETAILED DESCRIPTION

The object is solved by a preservative system which comprises a cationic surfactant, derived from the condensation of fatty acids and esterified dibasic amino acids, having the formula:

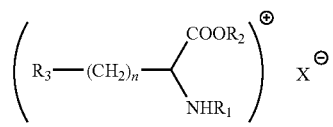

where:

$X^-$ is $Br^-$, $Cl^-$, or $HSO_4^-$ $R_1$: is a straight alkyl chain from an acid or saturated fatty hydroxy acid from 8 to 14 atoms of carbon bonded to the α-amino acid group through amidic bond, $R_2$: is a straight or branched alkyl chain from 1 to 18 carbon atoms or an aromatic group and $R_3$: is:

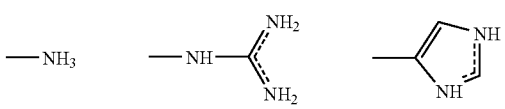

where n is from 0 to 4, and at least one other ionic or non-ionic preservative agent.

This preservative system is characterised for its synergetic activity. It has now been found that the antimicrobial activity of the combinations of LAE and the other compounds defined by the above formula (1) with most of the common ionic and non-ionic preservatives used to protect cosmetic formulations and preparations is higher than the activity displayed by each of the components when used alone at the same dosage. There has been observed synergism when the amounts of the compounds of formula (1) and the other antimicrobial are reduced. Thus, the adverse toxic effects and/or irritation and/or allergy displayed by the combinations of the preservatives have also been reduced.

It is a preferred embodiment of the preservative system of the invention when the cationic surfactant preservative derived from the condensation of fatty acids and esterified dibasic amino acid is LAE, since this compound displays the most effective properties with respect to the antimicrobial activity in the preservative system of the invention.

LAE can be used in association with other ionic preservatives, such as 2-bromo-2-nitro-1,3-propanediol (bronopol) and/or parabens and/or imidazolidinyl urea and/or 2-phenoxyethanol and/or 1,3-dimethylol-5,5-dimethylhydantoin and/or 2-methyl-5-chloro-3,4-isothiazolinone/2-methyl-3,4-isothiazolinone and/or quatemium-15, for cosmetic formulations and preparations that are applied to the epidermis, the capillary system, lips, nails, external genital organs, or on the teeth and in the mouth cavity mucous membranes, in order to clean, perfume, or modify their aspect and/or change body smells and/or protect a good physical state. At the same time, these preservative systems based on LAE protect against the growth of micro-organisms in the cosmetic formulations and preparations in which these are susceptible to grow, and against contamination with micro-organisms which are introduced without purpose by the customer during normal use.

The preservative system of the invention comprises the cationic surfactant of formula (1) in an amount from 0.001 to 2% by weight and the concentration of the other ionic or non ionic preservative agent from 0.0001% to 3% by weight relative to whole weight of the preservative system.

The preservative system of the invention comprises more in particular a preferred amount of the ionic or non-ionic preservative agent from 0.001 to 0.1% by weight of 2-bromo-2-nitro-1,3-propanediol (bronopol) and/or from 0.002 to 0.8% by weight of parabens and/or from 0.005 to 0.6% by weight of imidazolidinyl urea and/or from 0.01 to 1% by weight of 2-phenoxyethanol and/or from 0.003 to 0.6% by weight of 1,3-dimethylol-5,5-dimethylhydantoin and/or from 0.00015% to 0.0015% by weight of 2-methyl 5-chloro- 3,4-isothiazolinone /2-methyl-3,4-isothiazolinone and/or from 0.001 to 0.2% by weight of quaternium-15.

The composition of this invention comprises a medium which is compatible with the skin, the mucous membranes, and hair. These compositions may contain the usual components such as: fatty compounds such as mineral oil, animal oil, vegetal oil, from synthesis and silicon, and also alcohols, fatty acids and waxes; organic solvents, surface active agents, solubilizers and ionic and non ionic emulsifiers, thickening agents and jellying hydrophilic agents such as carboxyvinylic polymers (e.g. carbomer), acrylic copolymers (e.g. acrylates and alkylacrylates), polyacrylamides, polysaccharides, natural gums (e.g. xanthan gum); thickening agents and jellying lipophilic agents such as modified clays (ex. bentonite), fatty acid metallic salts, hydrophobic silica and polyethylene; perfumes and essential oils; softeners; excipients; antioxidants; sequestrant agents; opacifiers; filters; colouring compounds which are either hydrophilic or lipophilic, and pigments; and hydrophilic or lipophilic active ingredients. These compositions can also contain preservatives which are different from the ones defined in the claims.

The amounts of these usual components mentioned in the previous paragraph are the normal ones as used in the art. These components are added to the preservative systems of the invention without having any influence on their composition.

According to the invention the compositions can be in different cosmetic forms suitable for a topic application, such as:

a) Monophasic systems:
water or hydro-glycolic solution that contains one or more surfactants to be used for the cleaning of the skin, hair and mucous membranes;
water, hydro-alcoholic, hydro-glycolic or oily solution that can contain other additives to be used in the general care and/or protection for skin and/or mucous membranes;
water, hydro-alcoholic, hydro-glycolic or oily gel that can contain other additives to be used in general care and/or protection for skin and/or mucous membranes;
solid anhydride products that can contain other additives to be used in the general care and/or protection for skin and/or mucous membranes;

b) Biphasic systems:
water, hydro-alcoholic, hydro-glycolic or oily gel that can contain other additives to be used in general care and/or protection for skin and/or mucous membranes;
solid anhydride products that can contain other additives to be used in the general care and/or protection for skin and/or mucous membranes;
emulsions formed by dispersion of a oil phase in a water phase (OAW) or an inverse phase (W/O), to be used in general care and/or protection of the face skin, body, hands and/or mucous membranes; cleaning and/or removal of make-up from skin, mucous membranes, hair and/or mouth cavity; protection and/or skin care against solar radiation effects; colouring support and pigment to be applied to the skin;

c) and combinations of the other systems that form multiphasic systems, suspensions and microemulsions.

The compositions previously mentioned can also be used as a spray, or as aerosol compositions and can contain a propulsion agent under pressure.

Thus, the compositions of the invention can have the aspect of a cream, a lotion, a milk, an emulsion, a gel or an oil for the skin, a beauty mask, a salt, a gel, a foam/spray or an oil for a bath and shower, or for make-up and make-up cleaner of the face and eyes and anyway aspect to be shown.

The compositions according to the invention have been prepared according to usual techniques well known for an expert in the matter.

Procedure to Evaluate the Efficacy of the Preservative System

The method used to evaluate the efficacy is based on the *Antimicrobial Effectiveness Testing* USP $24^{th}$ Edition, 1999 (pp. 1809-1811), in order to demonstrate that the antimicrobial activity of the composition of the invention is effective in avoiding microbial growth which might be present during storage and use of the preparation, and preventing the adverse effects of the contamination (Real Farmacopea Española, $1^{st}$ Edición, 1997).

This assay consists on the contamination of the formulations to be protected with a mixed inoculum of $10^8$ cfu/ml concentration, in each of the micro-organisms, and see the variation of the viable cells in time. This mixed inoculum is composed of the following micro-organisms:

| | |
|---|---|
| *Pseudomonas aeruginosa* | ATCC 9027 |
| *Staphylococcus aureus* | ATCC 6538 |
| *Candida albicans* | ATCC 10231 |
| *Aspergillus niger* | ATCC 16404 |
| *Escherichia coli* | ATCC 8739 |

The cosmetic composition which is the subject of the investigation is divided into containers with 50 g of product for each flask. Each container is inoculated with 0.5 ml of the inoculum ($10^8$ cfu/ml). The target concentration is $10^6$ cfu/mL, approximately. All the containers are kept at a temperature between 20-25° C. and are protected against light.

The level of the microbial contamination is determined at 0 hours and after 7 days, 14 days and 28 days. The number of colonies is determined by dilution in buffer peptone with the appropriate neutraliser agent of the preservative. The culture media used for counting the micro-organisms were: Soya triptone agar (35-37° C., 48 hours) for the determination of bacteria; and Sabouraud agar with chloramphenicol for fungi and yeast (25° C., 3-5 days).

According to *Antimicrobial Effectiveness Testing* USP $24^{th}$ Edition, 1999 (pp. 1809-1811), an antimicrobial preservative is considered to be effective in topically used products made with aqueous bases or vehicles, non-sterile nasal products and emulsions, including those applied to mucous membranes, if:

not less than 2,0 logarithm reduction from the initial calculated bacteria's count at 14 days is reached and no increase from the 14 days' count is detected after 28 days; and no increase from the initial calculated count of yeast and moulds is observed.

EXAMPLES

Different examples of cosmetic preparation formulations according to the invention have been assayed. The displayed examples are only a selection, and do not represent a restriction to the use of the preservative system in other cases.

Example 1

The composition of the cosmetic formulation in oil in water emulsion with non-ionic surfactant, is (in g):

| | |
|---|---|
| Polysorbate 60 | 3.00 |
| Sorbitan stearate | 2.00 |
| Cetyl alcohol | 1.00 |

-continued

| | |
|---|---|
| Paraffin | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.25 |
| Carbomer 940 | 0.10 |
| Triethanolamine | 0.10 |
| Aqua | 100 c.s.p. |

This formulation is completed with a suitable amount of the preservative system of the invention and its capacity of preservation is evaluated against formulations with preservatives used alone.

The concentrations of the preservatives systems used in this example are shown in Table 1:

TABLE 1

| Preservative system | Composition |
|---|---|
| Blank | No preservative |
| 1 | LAE at 0.2% |
| 2 | 2-bromo-2-nitro-1,3-propanediol (bronopol) at 0.05% |
| 3 | methylchloroisothiazolinone/methylisothiazolinone at 0.0014% |
| 4 | 1,3-dimethylol-5,5-dimethylhydantoin at 0.22% |
| 5 | 2-phenoxyethanol at 0.5% |
| 6 | imidazolidinyl urea at 0.3% |
| 7 | parabens (methyl and propyl parabens) at 0.3% |
| 8 | quaternium-15 at 0.1% |
| 9 | LAE at 0.1% with 2-bromo-2-nitro-1,3-propanediol (bronopol) at 0.01% |
| 10 | LAE at 0.1% with 2-methyl-5-chloro-3,4-isothiazolinone/2-methyl-3,4-isothiazolinone at 0.0005% |
| 11 | LAE at 0.1% with 1,3-dimethylol-5,5-dimethylhydantoin at 0.11% |
| 12 | LAE at 0.1% with 2-phenoxyethanol at 0.17% |
| 13 | LAE at 0.1% with imidazolidinyl urea at 0.15%. |
| 14 | LAE at 0.1% with parabens (methyl and propyl parabens) at 0.16% |
| 15 | LAE at 0.1% with quaternium-15 at 0.03% |

The results are shown in the table 2.

After 28 days no increase was detected in comparison with the 14 days' count.

In the table 2 it is shown that the combination of LAE with other preservatives leads to effects which are regularly higher than those displayed by the common preservatives used alone, with the advantages described previously.

Example 2

The general composition of a cosmetic formulation in oil in water emulsion with an ionic emulsifier, is (in g):

| | |
|---|---|
| Stearic acid | 1.70 |
| Glyceryl stearate S.E. | 2.50 |
| Cetyl alcohol | 1.50 |
| Paraffin | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.50 |
| Triethanolamine | 1.03 |
| Aqua | 100 c.s.p. |

This formulation was completed with a suitable amount of the preservative system of the invention and its capacity of preservation was evaluated against the formulations with preservatives used alone.

The concentrations of the preservative systems used in this example are shown in Table 1.

TABLE 2

| Preservative system | Initial | | | 7 days | | | 14 days | | |
|---|---|---|---|---|---|---|---|---|---|
| | Aerobes | Fungi | Yeast | Aerobes | Fungi | Yeast | Aerobes | Fungi | Yeast |
| Blank | $2.1 \cdot 10^6$ | $1.6 \cdot 10^5$ | $8.7 \cdot 10^4$ | $2.1 \cdot 10^6$ | $7.0 \cdot 10^3$ | $8.2 \cdot 10^3$ | $6.2 \cdot 10^6$ | $5.9 \cdot 10^3$ | $4.8 \cdot 10^3$ |
| 1 | $1.1 \cdot 10^6$ | $1.7 \cdot 10^5$ | $5.6 \cdot 10^4$ | $3.1 \cdot 10^3$ | $8.9 \cdot 10^2$ | $9.5 \cdot 10^2$ | $3.3 \cdot 10^2$ | $<9.9 \cdot 10^1$ | $4.0 \cdot 10^2$ |
| 2 | $1.2 \cdot 10^6$ | $1.5 \cdot 10^5$ | $3.4 \cdot 10^4$ | $2.1 \cdot 10^3$ | $1.2 \cdot 10^3$ | $1.7 \cdot 10^2$ | $7.9 \cdot 10^2$ | $<9.9 \cdot 10^1$ | $<9.9 \cdot 10^1$ |
| 3 | $1.7 \cdot 10^6$ | $1.9 \cdot 10^5$ | $4.2 \cdot 10^4$ | $8.1 \cdot 10^2$ | $2.1 \cdot 10^3$ | $2.3 \cdot 10^2$ | $9.6 \cdot 10^2$ | $<9.9 \cdot 10^1$ | $<9.9 \cdot 10^1$ |
| 4 | $1.5 \cdot 10^6$ | $1.6 \cdot 10^5$ | $5.6 \cdot 10^4$ | $4.7 \cdot 10^3$ | $3.2 \cdot 10^3$ | $3.1 \cdot 10^2$ | $8.5 \cdot 10^2$ | $<9.9 \cdot 10^1$ | $<9.9 \cdot 10^1$ |
| 5 | $2.3 \cdot 10^6$ | $1.7 \cdot 10^5$ | $3.4 \cdot 10^4$ | $1.8 \cdot 10^3$ | $1.3 \cdot 10^3$ | $1.6 \cdot 10^2$ | $6.2 \cdot 10^2$ | $<9.9 \cdot 10^1$ | $<9.9 \cdot 10^1$ |
| 6 | $3.2 \cdot 10^6$ | $1.1 \cdot 10^5$ | $4.2 \cdot 10^4$ | $2.3 \cdot 10^3$ | $1.4 \cdot 10^3$ | $2.2 \cdot 10^2$ | $7.3 \cdot 10^2$ | $<9.9 \cdot 10^1$ | $<9.9 \cdot 10^1$ |
| 7 | $3.7 \cdot 10^6$ | $1.6 \cdot 10^5$ | $5.6 \cdot 10^4$ | $4.3 \cdot 10^3$ | $1.8 \cdot 10^3$ | $2.8 \cdot 10^2$ | $8.5 \cdot 10^2$ | $<9.9 \cdot 10^1$ | $<9.9 \cdot 10^1$ |
| 8 | $4.8 \cdot 10^6$ | $1.8 \cdot 10^5$ | $3.4 \cdot 10^4$ | $7.2 \cdot 10^3$ | $1.3 \cdot 10^3$ | $1.6 \cdot 10^2$ | $5.3 \cdot 10^2$ | $<9.9 \cdot 10^1$ | $<9.9 \cdot 10^1$ |
| 9 | $1.9 \cdot 10^6$ | $1.1 \cdot 10^5$ | $1.8 \cdot 10^4$ | $6.9 \cdot 10^2$ | $2.8 \cdot 10^2$ | $<9.9 \cdot 10^1$ | $1.9 \cdot 10^2$ | $<9.9 \cdot 10^1$ | $<9.9 \cdot 10^1$ |
| 10 | $3.6 \cdot 10^6$ | $1.1 \cdot 10^5$ | $1.6 \cdot 10^4$ | $9.6 \cdot 10^2$ | $3.3 \cdot 10^2$ | $<9.9 \cdot 10^1$ | $2.7 \cdot 10^2$ | $<9.9 \cdot 10^1$ | $<9.9 \cdot 10^1$ |
| 11 | $4.4 \cdot 10^6$ | $1.2 \cdot 10^5$ | $1.4 \cdot 10^4$ | $8.4 \cdot 10^2$ | $2.4 \cdot 10^2$ | $<9.9 \cdot 10^1$ | $1.6 \cdot 10^2$ | $<9.9 \cdot 10^1$ | $<9.9 \cdot 10^1$ |
| 12 | $2.1 \cdot 10^6$ | $1.1 \cdot 10^5$ | $2.2 \cdot 10^4$ | $9.1 \cdot 10^2$ | $3.9 \cdot 10^2$ | $<9.9 \cdot 10^1$ | $2.3 \cdot 10^2$ | $<9.9 \cdot 10^1$ | $<9.9 \cdot 10^1$ |
| 13 | $1.5 \cdot 10^6$ | $1.1 \cdot 10^5$ | $5.1 \cdot 10^4$ | $7.6 \cdot 10^2$ | $8.3 \cdot 10^2$ | $<9.9 \cdot 10^1$ | $1.8 \cdot 10^2$ | $<9.9 \cdot 10^1$ | $<9.9 \cdot 10^1$ |
| 14 | $1.8 \cdot 10^6$ | $1.3 \cdot 10^5$ | $2.1 \cdot 10^4$ | $9.4 \cdot 10^2$ | $7.9 \cdot 10^2$ | $<9.9 \cdot 10^1$ | $2.5 \cdot 10^2$ | $<9.9 \cdot 10^1$ | $<9.9 \cdot 10^1$ |
| 15 | $2.2 \cdot 10^6$ | $1.1 \cdot 10^5$ | $3.3 \cdot 10^4$ | $8.3 \cdot 10^2$ | $6.3 \cdot 10^2$ | $<9.9 \cdot 10^1$ | $2.7 \cdot 10^2$ | $<9.9 \cdot 10^1$ | $<9.9 \cdot 10^1$ |

The results are shown in the table 3.

TABLE 3

| Preservative system | Initial | | | 7 days | | | 14 days | | |
|---|---|---|---|---|---|---|---|---|---|
| | Aerobes | Fungi | Yeast | Aerobes | Fungi | Yeast | Aerobes | Fungi | Yeast |
| Blank | $7.4 \cdot 10^6$ | $2.0 \cdot 10^5$ | $3.6 \cdot 10^4$ | $5.2 \cdot 10^6$ | $4.9 \cdot 10^3$ | $4.7 \cdot 10^4$ | $1.7 \cdot 10^7$ | $3.8 \cdot 10^4$ | $1.0 \cdot 10^4$ |
| 1 | $2.7 \cdot 10^6$ | $1.4 \cdot 10^5$ | $3.6 \cdot 10^4$ | $1.6 \cdot 10^4$ | $7.2 \cdot 10^3$ | $1.0 \cdot 10^2$ | $6.5 \cdot 10^2$ | $2.8 \cdot 10^2$ | $1.0 \cdot 10^2$ |
| 2 | $4.5 \cdot 10^6$ | $1.5 \cdot 10^5$ | $2.9 \cdot 10^4$ | $2.1 \cdot 10^4$ | $8.5 \cdot 10^3$ | $8.9 \cdot 10^2$ | $3.8 \cdot 10^3$ | $1.1 \cdot 10^2$ | $4.0 \cdot 10^2$ |
| 3 | $6.3 \cdot 10^6$ | $1.8 \cdot 10^5$ | $2.7 \cdot 10^4$ | $8.1 \cdot 10^3$ | $5.7 \cdot 10^3$ | $4.3 \cdot 10^2$ | $9.7 \cdot 10^2$ | $2.6 \cdot 10^2$ | $<9.9 \cdot 10^1$ |
| 4 | $5.2 \cdot 10^6$ | $1.4 \cdot 10^5$ | $1.8 \cdot 10^4$ | $4.7 \cdot 10^3$ | $6.2 \cdot 10^3$ | $2.8 \cdot 10^2$ | $8.7 \cdot 10^2$ | $2.7 \cdot 10^2$ | $<9.9 \cdot 10^1$ |
| 5 | $2.7 \cdot 10^6$ | $1.2 \cdot 10^5$ | $2.3 \cdot 10^4$ | $1.8 \cdot 10^4$ | $5.5 \cdot 10^3$ | $5.3 \cdot 10^2$ | $1.8 \cdot 10^3$ | $3.4 \cdot 10^2$ | $<9.9 \cdot 10^1$ |
| 6 | $1.8 \cdot 10^6$ | $1.3 \cdot 10^5$ | $3.3 \cdot 10^4$ | $2.3 \cdot 10^4$ | $7.3 \cdot 10^3$ | $4.3 \cdot 10^2$ | $9.2 \cdot 10^2$ | $2.7 \cdot 10^2$ | $<9.9 \cdot 10^1$ |
| 7 | $3.9 \cdot 10^6$ | $1.6 \cdot 10^5$ | $3.2 \cdot 10^4$ | $4.3 \cdot 10^4$ | $6.8 \cdot 10^3$ | $6.7 \cdot 10^2$ | $1.3 \cdot 10^3$ | $3.8 \cdot 10^2$ | $<9.9 \cdot 10^1$ |
| 8 | $4.6 \cdot 10^6$ | $1.8 \cdot 10^5$ | $1.9 \cdot 10^4$ | $7.2 \cdot 10^3$ | $5.3 \cdot 10^3$ | $5.9 \cdot 10^2$ | $9.8 \cdot 10^2$ | $<9.9 \cdot 10^1$ | $<9.9 \cdot 10^1$ |
| 9 | $2.4 \cdot 10^6$ | $1.7 \cdot 10^5$ | $2.5 \cdot 10^4$ | $6.9 \cdot 10^3$ | $.9 \cdot 10^3$ | $4.8 \cdot 10^2$ | $3.8 \cdot 10^2$ | $<9.9 \cdot 10^1$ | $<9.9 \cdot 10^1$ |
| 10 | $2.6 \cdot 10^6$ | $1.9 \cdot 10^5$ | $2.1 \cdot 10^4$ | $9.6 \cdot 10^3$ | $1.8 \cdot 10^3$ | $3.3 \cdot 10^2$ | $9.6 \cdot 10^2$ | $<9.9 \cdot 10^1$ | $<9.9 \cdot 10^1$ |
| 11 | $1.7 \cdot 10^6$ | $2.4 \cdot 10^5$ | $3.1 \cdot 10^4$ | $8.4 \cdot 10^3$ | $1.3 \cdot 10^3$ | $5.4 \cdot 10^2$ | $9.2 \cdot 10^2$ | $<9.9 \cdot 10^1$ | $<9.9 \cdot 10^1$ |
| 12 | $1.4 \cdot 10^6$ | $2.7 \cdot 10^5$ | $3.6 \cdot 10^4$ | $9.1 \cdot 10^3$ | $2.4 \cdot 10^3$ | $<9.9 \cdot 10^1$ | $3.7 \cdot 10^3$ | $<9.9 \cdot 10^1$ | $<9.9 \cdot 10^1$ |
| 13 | $2.1 \cdot 10^6$ | $1.1 \cdot 10^5$ | $3.6 \cdot 10^4$ | $7.6 \cdot 10^3$ | $3.9 \cdot 10^3$ | $1.6 \cdot 10^2$ | $9.6 \cdot 10^2$ | $<9.9 \cdot 10^1$ | $<9.9 \cdot 10^1$ |
| 14 | $1.4 \cdot 10^6$ | $3.7 \cdot 10^5$ | $3.3 \cdot 10^4$ | $9.4 \cdot 10^3$ | $1.9 \cdot 10^3$ | $1.3 \cdot 10^2$ | $1.4 \cdot 10^3$ | $<9.9 \cdot 10^1$ | $<9.9 \cdot 10^1$ |
| 15 | $2.1 \cdot 10^6$ | $2.4 \cdot 10^5$ | $3.4 \cdot 10^3$ | $8.3 \cdot 10^3$ | $2.9 \cdot 10^3$ | $1.4 \cdot 10^2$ | $7.1 \cdot 10^2$ | $<9.9 \cdot 10^1$ | $<9.9 \cdot 10^1$ |

After 28 days no increase was detected from the 14 days' count.

In the table 3 is shown that the combination of the LAE with other preservatives is equal or higher than the common preservatives used alone, with the advantages described previously Example 3

The general composition of a cosmetic formulation containing a water in oil emulsion with non-ionic emulsifier, is (in g)

| | |
|---|---|
| Cetyl Dimethicone copolyol | 3.00 |
| Isohexadecane | 6.00 |

-continued

| | |
|---|---|
| Paraffin | 8.00 |
| Isopropyl myristate | 6.00 |
| Caprylic-caproic triglycerides | 4.00 |
| Glycerol | 5.00 |
| Sodium chloride | 0.50 |
| Aqua | 100 c.s.p. |

This formulation was completed with the suitable amount of the preservative system of the invention and its capacity of preservation was evaluated against the formulations with preservatives used alone.

The concentrations of the preservatives systems used in this example are shown in Table 1.

The results are shown in the Table 4.

| Preservative system | Initial | | | 7 days | | | 14 days | | |
|---|---|---|---|---|---|---|---|---|---|
| | Aerobes | Fungi | Yeast | Aerobes | Fungi | Yeast | Aerobes | Fungi | Yeast |
| Blank | $5.6 \cdot 10^6$ | $2.0 \cdot 10^5$ | $8.8 \cdot 10^4$ | $1.1 \cdot 10^6$ | $5.0 \cdot 10^4$ | $9.0 \cdot 10^3$ | $8.7 \cdot 10^6$ | $9.2 \cdot 10^3$ | $6.0 \cdot 10^3$ |
| 1 | $6.2 \cdot 10^6$ | $1.0 \cdot 10^5$ | $7.0 \cdot 10^4$ | $1.8 \cdot 10^3$ | $<9.9 \cdot 10^1$ | $<9.9 \cdot 10^1$ | $<9.9 \cdot 10^1$ | $<9.9 \cdot 10^1$ | $<9.9 \cdot 10^1$ |
| 2 | $3.3 \cdot 10^6$ | $3.5 \cdot 10^4$ | $5.9 \cdot 10^4$ | $5.7 \cdot 10^3$ | $8.5 \cdot 10^3$ | $8.9 \cdot 10^2$ | $2.8 \cdot 10^3$ | $<9.9 \cdot 10^1$ | $4.0 \cdot 10^2$ |
| 3 | $4.3 \cdot 10^6$ | $4.8 \cdot 10^4$ | $2.7 \cdot 10^4$ | $6.1 \cdot 10^3$ | $5.7 \cdot 10^3$ | $4.3 \cdot 10^2$ | $8.1 + 02$ | $<9.9 \cdot 10^1$ | $<9.9 \cdot 10^1$ |
| 4 | $5.6 \cdot 10^6$ | $6.4 \cdot 10^4$ | $4.8 \cdot 10^4$ | $4.7 \cdot 10^3$ | $6.2 \cdot 10^3$ | $2.8 \cdot 10^2$ | $4.3 \cdot 10^2$ | $<9.9 \cdot 10^1$ | $<9.9 \cdot 10^1$ |
| 5 | $4.8 \cdot 10^6$ | $4.2 \cdot 10^4$ | $5.3 \cdot 10^4$ | $3.9 \cdot 10^3$ | $5.5 \cdot 10^3$ | $5.3 \cdot 10^2$ | $1.9 \cdot 10^3$ | $<9.9 \cdot 10^1$ | $<9.9 \cdot 10^1$ |
| 6 | $3.7 \cdot 10^6$ | $4.3 \cdot 10^4$ | $6.3 \cdot 10^4$ | $4.2 \cdot 10^3$ | $6.3 \cdot 10^3$ | $4.3 \cdot 10^2$ | $8.6 \cdot 10^2$ | $<9.9 \cdot 10^1$ | $<9.9 \cdot 10^1$ |
| 7 | $3.1 \cdot 10^6$ | $5.6 \cdot 10^4$ | $5.2 \cdot 10^4$ | $4.6 \cdot 10^3$ | $4.8 \cdot 10^3$ | $6.7 \cdot 10^2$ | $1.1 \cdot 10^3$ | $<9.9 \cdot 10^1$ | $<9.9 \cdot 10^1$ |
| 8 | $4.2 \cdot 10^6$ | $3.8 \cdot 10^4$ | $5.9 \cdot 10^4$ | $2.7 \cdot 10^3$ | $1.3 \cdot 10^3$ | $5.9 \cdot 10^2$ | $9.4 \cdot 10^2$ | $<9.9 \cdot 10^1$ | $<9.9 \cdot 10^1$ |
| 9 | $5.1 \cdot 10^6$ | $2.7 \cdot 10^4$ | $4.6 \cdot 10^4$ | $7.8 \cdot 10^2$ | $7.9 \cdot 10^2$ | $4.8 \cdot 10^2$ | $7.9 \cdot 10^2$ | $<9.9 \cdot 10^1$ | $<9.9 \cdot 10^1$ |
| 10 | $2.3 \cdot 10^6$ | $2.9 \cdot 10^4$ | $3.7 \cdot 10^4$ | $9.2 \cdot 10^2$ | $4.9 \cdot 10^2$ | $3.3 \cdot 10^2$ | $6.5 \cdot 10^2$ | $<9.9 \cdot 10^1$ | $<9.9 \cdot 10^1$ |
| 11 | $1.8 \cdot 10^6$ | $1.4 \cdot 10^4$ | $4.9 \cdot 10^4$ | $7.3 \cdot 10^2$ | $3.9 \cdot 10^2$ | $5.4 \cdot 10^2$ | $5.4 \cdot 10^2$ | $<9.9 \cdot 10^1$ | $<9.9 \cdot 10^1$ |
| 12 | $1.2 \cdot 10^6$ | $2.7 \cdot 10^4$ | $4.6 \cdot 10^4$ | $9.2 \cdot 10^2$ | $2.9 \cdot 10^2$ | $<9.9 \cdot 10^1$ | $6.7 \cdot 10^2$ | $<9.9 \cdot 10^1$ | $<9.9 \cdot 10^1$ |
| 13 | $2.1 \cdot 10^6$ | $1.8 \cdot 10^4$ | $3.9 \cdot 10^4$ | $8.6 \cdot 10^2$ | $4.9 \cdot 10^2$ | $1.6 \cdot 10^2$ | $5.5 \cdot 10^2$ | $<9.9 \cdot 10^1$ | $<9.9 \cdot 10^1$ |
| 14 | $2.2 \cdot 10^6$ | $2.6 \cdot 10^4$ | $3.3 \cdot 10^4$ | $9.4 \cdot 10^2$ | $2.9 \cdot 10^2$ | $1.3 \cdot 10^2$ | $8.6 \cdot 10^2$ | $<9.9 \cdot 10^1$ | $<9.9 \cdot 10^1$ |
| 15 | $2.4 \cdot 10^6$ | $4.1 \cdot 10^4$ | $3.4 \cdot 10^4$ | $8.3 \cdot 10^2$ | $3.9 \cdot 10^2$ | $1.4 \cdot 10^2$ | $6.7 \cdot 10^2$ | $<9.9 \cdot 10^1$ | $<9.9 \cdot 10^1$ |

After 28 days no increase was been detected from the 14 days' count.

In the table 4 it is shown that the combination of the LAE with other preservatives is equal or higher than the common preservatives used alone, with the advantages described previously Further formulations 4 to 15 are described hereafter. The experimental results obtained in the examples 1 to 3 are representative for the examples 1 to 15.

Example 4

The composition of a formulation to obtain an aqueous solution with a mixture of surfactants, is (in g):

| | |
|---|---|
| Sodium lauryl sulfate (sol. 27%) | 14.00 |
| Cocamidopropyl betaine | 6.00 |
| Disodium cocoamfoacetate | 6.00 |
| Lactic acid | 0.25 |
| Sodium chloride | 0.50 |
| Aqua | 100 c.s.p. |

This formulation is applied in bath gels.

Example 5

The composition of a formulation to obtain an aqueous solution with a mixture of surfactants, is (in g):

| | |
|---|---|
| Sodium lauryl sulfate (sol. 27%) | 14.00 |
| Cocamidopropyl betaine | 6.00 |
| Disodium laureth sulfosuccinate | 6.00 |
| Lactic acid | 0.25 |
| Sodium chloride | 0.50 |
| Aqua | 100 c.s.p. |

This formulation is applied in bath gels.

Example 6

The composition of a formulation to obtain a hydro-alcoholic gel, is (in g):

| | |
|---|---|
| Hydroxyethyl cellulose | 0.40 |
| Carbomer 940 | 0.40 |
| Glycerol | 8.00 |
| Alcohol denat | 30.00 |
| PEG 40 hydrogenated castor oil | 1.50 |
| Parfum | 0.75 |
| Triethanolamine | 0.25 |
| Aqua | 100 c.s.p. |

This formulation is applied in lotions for skin care after shaving.

Example 7

The composition of a formulation to obtain a tonic for the face, is (in g):

| | |
|---|---|
| Hydroxyethyl cellulose | 0.20 |
| Caprylic-caproic triglycerides | 1.00 |
| PEG 40 hydrogenated castor oil | 6.00 |
| Lactic acid | 1.00 |
| Sodium chloride | 0.35 |
| Glycerol | 3.00 |
| Chamomilla Recutita extract | 3.00 |
| Aqua | 100 c.s.p. |

Example 8

The composition of a formulation to obtain a mask-up cleaner, is (in g):

| | |
|---|---|
| Stearic acid | 2.00 |
| Glyceryl stearate S.E. | 2.50 |
| Cetyl alcohol | 1.50 |
| Paraffin | 6.00 |
| Isopropyl myristate | 1.50 |
| Caprylic-caproic triglycerides | 1.50 |
| Dimethicone | 0.50 |
| Propylene glycol | 3.00 |
| Triethanolamine | 1.20 |
| Aqua | 100 c.s.p. |

Example 9

The composition of a formulation to obtain a fluid oil-in-water emulsion with non-ionic surfactants, is (in g):

| | |
|---|---|
| Polysorbate 60 | 3.00 |
| Sorbitan stearate | 2.00 |
| Cetyl alcohol | 0.75 |
| Paraffin | 3.00 |
| Isopropyl myristate | 2.50 |
| Caprylic-caproic triglycerides | 2.00 |
| Dimethicone | 0.50 |
| Propylene glycol | 3.00 |
| Aqua | 100 c.s.p. |

This formulation is applied as a body oil.

Example 10

The composition of a toothpaste formulation is (in g):

| | |
|---|---|
| Calcium carbonate | 16.00 |
| Dicalcium phosphate | 24.00 |
| Silica | 2.00 |
| Petrolatum | 10.00 |
| Glycerol | 20.00 |
| Sodium fluoride | 0.20 |
| Hydroxyethyl cellulose | 1.00 |
| Lauroyl sarcosine | 2.00 |
| Aqua | 100 c.s.p. |

Example 11

The composition to obtain an aqueous solution with surfactants, is (in g):

| | |
|---|---|
| Sodium lauryl sulfate (sol. 27%) | 12.00 |
| Cocamidopropyl betaine | 5.00 |
| Disodium cocoamfoacetate | 5.00 |
| Polyquaternium11 | 1.00 |
| Lactic acid | 0.25 |
| Sodium chloride | 0.50 |
| Aqua | 100 c.s.p. |

This formulation is applied as a shampoo.

Example 12

The composition of a formulation to obtain an oil-in-water emulsion with non-ionic surfactants, is (in g):

| | |
|---|---|
| Glyceryl stearate + PEG 100 stearate | 4.00 |
| Cetyl alcohol + sodium cetyl sulfate | 2.00 |
| Caprylic-caproic triglycerides | 4.00 |
| Isopropyl myristate | 2.50 |
| Paraffin | 2.00 |
| Dimethicone | 0.50 |
| Glycerol | 3.00 |
| Wheat (triticum vulgare) germ protein | 2.00 |
| Aqua | 100 c.s.p. |

This formulation is applied as a face cream for skin care.

Example 13

The composition of a formulation to obtain an oil-in-water emulsion with non-ionic surfactants, is (in g):

| | |
|---|---|
| Polysorbate 60 | 3.00 |
| Sorbitan stearate | 2.00 |
| Cetyl alcohol | 2.50 |
| Paraffin | 2.00 |
| Caprylic-caproic triglycerides | 2.00 |
| Ethyl hexyl methoxycinnamate | 5.00 |
| Benzophenone 3 | 1.00 |
| Dimethicone | 0.50 |
| Propylene glycol | 3.00 |
| Aqua | 100 c.s.p. |

This formulation is applied as a sun protector.

Example 14

The composition of a formulation to obtain an oil in water emulsion with non-ionic surfactants is (in g):

| | |
|---|---|
| Cetyl Dimethicone copolyol | 3.00 |
| Isohexadecane | 4.00 |
| Paraffin | 5.00 |
| Isopropyl myristate | 3.00 |
| Caprylic-caproic triglycerides | 3.00 |
| Ethyl hexyl methoxycinnamate | 5.00 |
| Benzophenone 3 | 1.00 |
| Glycerol | 3.00 |
| Sodium chloride | 0.50 |
| Aqua | 100 c.s.p. |

This formulation is applied as a sun protector cosmetic product.

Example 15

The composition of a formulation to obtain an emulsion for hands care, is (in g):

| | |
|---|---|
| Cetyl alcohol + ceteareth 20 | 6.00 |
| Isopropyl myristate | 2.00 |
| Caprylic-caproic triglycerides | 1.00 |
| Dimethicone | 1.00 |
| Benzophenone 3 | 1.00 |
| Glycerol | 6.00 |
| Carbomer 940 | 0.10 |
| Triethanolamine | 0.10 |
| Aqua | 100 c.s.p. |

The invention claimed is:

1. A cosmetic or dermatological composition containing a preservative system comprising
   (a) 0.001 to 2% by weight of a cationic surfactant, derived from the condensation of fatty acids and esterified dibasic amino acids, having the formula:

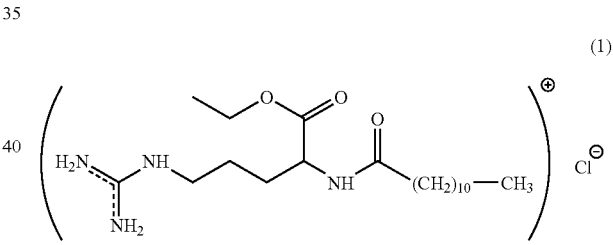

and
   (b) at least one other ionic or non-ionic preservative agent chosen from 0.002 to 0.8% by weight of parabens, from 0.005 to 0.6% by weight of imidazolidinyl urea, from 0.01 to 1% by weight of 2-phenoxyethanol, from 0.003 to 0.6% by weight of 1,3-dimethylol-5,5-dimethylhydantoin, from 0.00015% to 0.0015% by weight of 2-methyl 5-chloro 3,4-isothiazolinone/2-methyl 3,4-isothiazolinone, from 0.001 to 0.2% by weight of quaternium-15, or mixtures of two or more thereof, wherein (a) and (b) are present in a combined amount synergistically effective to control the growth of microorganisms.

2. The composition of claim 1, further comprising one or more: fatty compounds selected from mineral oil, animal oil, vegetal oil, fatty alcohols, fatty acids and waxes; organic solvents; surface active agents; solubilizers and ionic and non-ionic emulsifiers; thickening agents and jellying hydrophilic agents selected from carboxyvinylic polymers, acrylic copolymers, polyacrylamides, polysaccharides and natural gums; thickening agents and jellying lipophilic agents selected from modified clays, fatty acid metallic salts; hydrophobic silica and polyethylene; perfumes and essential oils, softeners, excipients, antioxidants, sequestrants; opacifiers; filters; coloring compounds and pigments; or hydrophilic or lipophilic active ingredients.

3. The composition of claim 2, wherein the composition which contains the preservative system of claim 1 is one or more of a cream, emulsion, lotion, gel, oil, beauty mask, bath product, shower product, make-up, make-up cleaner or make-up remover.

4. The composition of claim 2, wherein the composition is an aqueous solution, hydro-alcoholic, hydro-glycolic emulsion, micro-emulsion, aqueous or anhydride gel of a vesicles dispersion.

5. A method of using a preservative system, the method comprising the step of using the composition of claim 1 to avoid microbial growth.

6. A method of using a preservative system, the method comprising the step of using the composition of claim 1 to protect against at least one microbial organism in the composition.

7. The composition of claim 1, wherein the composition is one or more of a cream, emulsion, lotion, gel, oil, beauty mask, bath product, shower product, make-up, make-up cleaner or make-up remover.

8. The composition of claim 1, wherein the composition is an aqueous solution, hydro-alcoholic, hydro-glycolic emulsion, micro-emulsion, aqueous or anhydride gel of a vesicles dispersion.

9. A method of using a composition, the method comprising the step of using the composition comprising the preservative system of claim 1 to avoid microbial growth.

10. A method of using a composition, the method comprising the step of using the composition comprising the preservative system of claim 1 to protect against at least one microbial organism in the cosmetic or dermatological composition.

* * * * *